(12) United States Patent
Wood et al.

(10) Patent No.: US 10,482,998 B2
(45) Date of Patent: Nov. 19, 2019

(54) CELL PROCESSING TECHNIQUES

(71) Applicant: General Electric Company, Schenectady, NY (US)

(72) Inventors: Nichole Lea Wood, Niskayuna, NY (US); Lynn Ann DeRose, Gloversville, NY (US); Brandon Stephen Good, Schenectady, NY (US); Adam Joseph McCann, Schenectady, NY (US); Hasan Imamus Saleheen, Marlborough, MA (US)

(73) Assignee: General Electric Company, Schenectady, NY (US)

( * ) Notice: Subject to any disclaimer, the term of this patent is extended or adjusted under 35 U.S.C. 154(b) by 724 days.

(21) Appl. No.: 14/984,574

(22) Filed: Dec. 30, 2015

(65) Prior Publication Data
US 2017/0193167 A1   Jul. 6, 2017

(51) Int. Cl.
*G16H 10/40* (2018.01)
*G16H 10/65* (2018.01)
*G16H 10/60* (2018.01)
*H04B 5/00* (2006.01)

(52) U.S. Cl.
CPC ............. *G16H 10/40* (2018.01); *G16H 10/60* (2018.01); *G16H 10/65* (2018.01); *H04B 5/0062* (2013.01)

(58) Field of Classification Search
CPC ................................ G16H 10/40; G16H 10/60
See application file for complete search history.

(56) References Cited

U.S. PATENT DOCUMENTS

| | | | |
|---|---|---|---|
| 6,976,033 | B2 | 12/2005 | Yang et al. |
| 7,844,349 | B2 | 11/2010 | Weatherhead et al. |
| 8,046,588 | B2 | 10/2011 | Gibart et al. |
| 8,982,156 | B2 | 3/2015 | Maggiore |
| 9,046,882 | B2 | 6/2015 | Bartee et al. |
| 9,050,379 | B2 | 6/2015 | Selker et al. |

(Continued)

FOREIGN PATENT DOCUMENTS

| | | |
|---|---|---|
| CN | 1745735 A | 3/2006 |
| EP | 0946921 B1 | 9/2001 |

OTHER PUBLICATIONS

Brindley, David A., et al.; "Automation of Cell Therapy Biomanufacturing", BioProcess International, vol. 11, Sup. 1, Mar. 2013.

(Continued)

*Primary Examiner* — Jonathan Durant
(74) *Attorney, Agent, or Firm* — Eversheds Sutherland (US) LLP (57) ABSTRACT

The present disclosure relates to cell processing techniques. By way of example, a cell processing system may include a plurality of tracking devices coupled to a respective plurality of sample processing containers and storing sample identification information for a patient sample for use with sample processing devices configured to process the patient sample according to workflow steps of a processing protocol. A plurality of readers are configured to receive signals from the plurality of tracking devices. A controller may be coupled to the plurality of readers and configured to determine if the patient sample is processed according to the processing protocol based at least in part on the signals from the plurality of tracking devices.

13 Claims, 10 Drawing Sheets

(56) References Cited

U.S. PATENT DOCUMENTS

| | | | |
|---|---|---|---|
| 2008/0109100 A1 | 5/2008 | Macharia et al. | |
| 2008/0305515 A1* | 12/2008 | Burgart | G01N 1/312 435/40.52 |
| 2009/0071829 A1* | 3/2009 | O'Banion | B01L 3/545 204/461 |
| 2010/0126286 A1* | 5/2010 | Self | G01N 35/04 73/863.81 |
| 2011/0115633 A1* | 5/2011 | Morris | B01L 3/5027 340/572.8 |
| 2012/0025985 A1* | 2/2012 | Bolander | G16H 10/40 340/572.1 |
| 2012/0029832 A1* | 2/2012 | Dodgson | B01L 3/50825 702/19 |
| 2015/0039342 A1 | 2/2015 | Chen et al. | |
| 2017/0193168 A1 | 7/2017 | Lea et al. | |

OTHER PUBLICATIONS

Trakcel, "Applications across the cell therapy supply chain", retrieved from "https://trakcel.com/overview.html#ov-manufacturing" on Mar. 29, 2016.

Stone, Edwin; "Technological Advances Facilitate Autologous Cell Therapy Scale-Out", Genetic Engineering & Biotechnology News, Aug. 25, 2015, retrieved from "http://www.genengnews.com/insight-and-intelligence/ technological-advances-facilitate-autologous-cell-therapy-scale/77900512/?kwrd=Regenerative%20Medicine" on Mar. 29, 2016.

Petrides, Demetri, et al.; "Biopharmaceutical Process Optimization with Simulation and Scheduling Tools", Bioengineering vol. 1, pp. 154-187, 2014.

Chen, R.C., et al., "An RFID-based enterprise application integration framework for real-time management of dynamic manufacturing processes," The international journal of Advanced Manufacturing Technology, vol. 50, Issue. 9-12, pp. 1217-1234 (2010).

International Search Report and Written Opinion issued in connection with corresponding PCT Application No. PCT/EP2016/082122 dated Apr. 4, 2017.

Ghouze, F., et al., Parallel Cell Processing Merthod and Facility, GE co-pending U.S. Appl. No. 62/026,748, filed Jul. 21, 2014.

Vanek, P., et al., Cell Processing Method, GE co-pending U.S. Appl. No. 62/026,762, filed Jul. 21, 2014.

* cited by examiner

CELL PROCESSING TECHNIQUES

BACKGROUND

The subject matter disclosed herein relates to cell therapy techniques for processing and delivering cells to a therapy patient.

In autologous cellular immunotherapies, a patient's own blood, fluid, tissue, or cell sample is typically collected in a hospital/clinical setting and transferred to a central location for manufacturing of a cellular therapy generated from and/or based on the collected sample. The cellular therapy product is then delivered back to a clinical setting for infusion into same patient. Once at the processing location, the production of the therapy from the sample typically takes several days (e.g., 3-10 days) and may involve manual processing steps within the processing facility. Tracking each patient's sample from the collection point and before, during, and after processing to the delivery point introduces additional complexity into an already extensive process.

BRIEF DESCRIPTION

In one embodiment, a cell processing tracking system is provided. The system includes a sample container configured to hold a cell therapy sample; a reader co-located with a sample processing location and configured to receive an identification signal from a tracking device coupled to the sample container; a controller operatively coupled to the receiver and configured to: access a processing protocol associated with the identification signal upon receipt of the identification signal; determine if the cell therapy sample is being processed according to the processing protocol; provide an error signal when the cell therapy sample is not being processed according to the processing protocol; and provide a verification signal when the cell therapy sample is being processed according to the processing protocol In another embodiment, a cell processing method is provided. The method includes the step of receiving at a processing facility a patient sample from a collection facility, wherein the patient sample is associated with sample identification information. The method also includes the steps of providing a plurality of tracking devices coupled to a respective plurality of sample processing containers, wherein each tracking device stores the sample identification information and processing the patient sample to generate a processed patient sample using the plurality of sample processing containers according to a processing protocol having a plurality of workflow steps. The method also includes the steps of capturing the identification information from the plurality of sample processing containers while processing the patient sample using a plurality of readers associated with respective workflow steps; determining that patient sample is processed according to the processing protocol at each workflow step based on the captured sample identification information from the plurality of readers; providing a visual indication at a location associated with each workflow step that the patient sample is processed according to the processing protocol; and providing the processed patient sample to the collection facility.

In another embodiment, a cell processing system is provided. The system includes a plurality of tracking devices coupled to a respective plurality of sample processing containers, wherein each tracking device stores the sample identification information for a patient sample; a plurality of sample processing devices configured to process the patient sample to generate a processed patient sample using the plurality of sample processing containers according to a processing protocol having a plurality of workflow steps; a plurality of readers respectively co-located with the plurality of sample processing devices and configured to receive signals from the plurality of tracking devices; and a controller coupled to the plurality of readers and configured to determine if the patient sample is processed according to the processing protocol based at least in part on the signals from the plurality of tracking devices.

In another embodiment, a device is provided. The device includes a housing; an audio or visual notification device disposed in or on the housing and comprising one or more of a light source or a speaker; a transceiver disposed in or on the housing and configured to receive signals from a tracking device coupled to a sample processing container holding a patient sample; communications circuitry disposed in or on the housing and configured to communicate the signals to a central controller and receive instructions associated with an error or a verification of a processing protocol for the patient sample from the central controller based on the signals; and a processor disposed in or on the housing and configured to activate the audio or visual notification device to turn on the one or more light sources or emit a sound from the speaker associated with an error based on the instructions associated with the error.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

In cell therapy applications, a cell therapy sample is processed according to a manufacturing or processing protocol that depends on the cell type, the patient clinical condition, the desired therapy, the condition of the sample, and other factors. Typically, one or very few samples are processed in a given processing area, and the sample identity and protocol followed are documented manually at each step to prevent sample and/or protocol errors. Further, there is often an assigned person whose job is to shadow the operator and verify that the correct sample is processed in the correct way following the standard operating protocol (SOP). Accordingly, sample processing can be very low throughput and labor intensive. Further, manual or handwritten documentation can be challenging when operating in clean room environments requiring operators to be fully gowned in personal protective equipment to maintain room sterility. As the number of patient samples per location increases due to demand for autologous therapies, increased throughput will be desirable. However, the use of human verification and the processing space required to minimize sample mix-up will make scale-up of the process a challenge.

Provided herein are techniques for improved processing of cell therapy samples, e.g., autologous cell therapy, that permit tracking of consumable bags, operators, and equipment use in order to monitor real-time the compliance with an electronic standard operating protocol (SOP) and provide electronic and visual notification when a deviation has occurred, providing opportunity for operator to correct the deviation real-time. In addition, if the error notification is not sufficient, additional feedback may control the processing equipment and may prevent operation when an error is detected and prevent further operation until the error is corrected. Such techniques may be used to improve throughput of cell therapy samples while ensuring correct processing, by reducing the complexity of verification steps.

While certain embodiments of the disclosure are directed towards autologous cell therapies that involve collection, manipulation, and re-insertion of a patient's own cells, the applications of the disclosed techniques may include allogenic cells, modified human cells, or xenotransplantation of non-human cells. Cell based therapies that are contemplated as being used in conjunction with the disclosed techniques may include therapies for organ or tissue regeneration, cancer treatment, blood disorders, immunotherapies, heart disease, or any other cell-based therapies.

Figure 1:
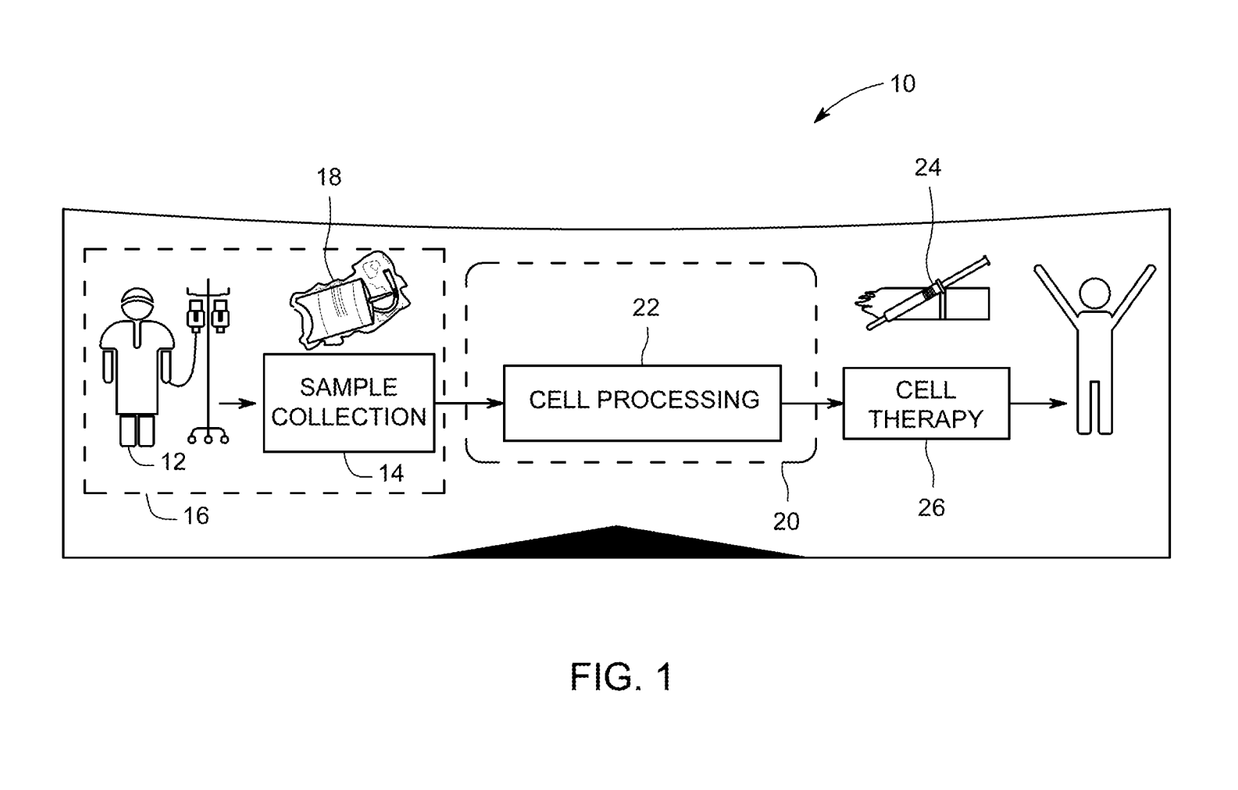
FIG. 1 is a schematic representation of a cell therapy treatment according to an embodiment of the present disclosure.

FIG. 1 is a schematic representation of an autologous cell therapy technique 10. A patient 12 in need of cell therapy treatment is scheduled for sample collection 14 at a collection facility 16, typically a hospital or outpatient treatment facility. The collected sample 18, which may be a blood, tissue, urine, or other biological sample, is then provided to a cell therapy processing facility 20, where the collected sample 18 undergoes appropriate processing via a cell processing protocol 22 to generate a cell therapy product 24. However, in certain embodiments, the collected sample 18 is processed at a point-of-care facility co-located with the collection facility 16. The manufactured cell therapy product 24 is then used in a cell therapy treatment 26 for the patient 12. For example, the cell therapy product may be injected into the patient's vein. Before the cell therapy product 24 is provided for cell therapy treatment 26, the cell therapy product 24 may be assessed for cellular product quality and adherence to regulatory (e.g., FDA) requirements. For example, such requirements may include sterility, a particular cell count, or a particular fraction of viable cells, e.g., a minimum cell viability of 70%.

Figure 2:
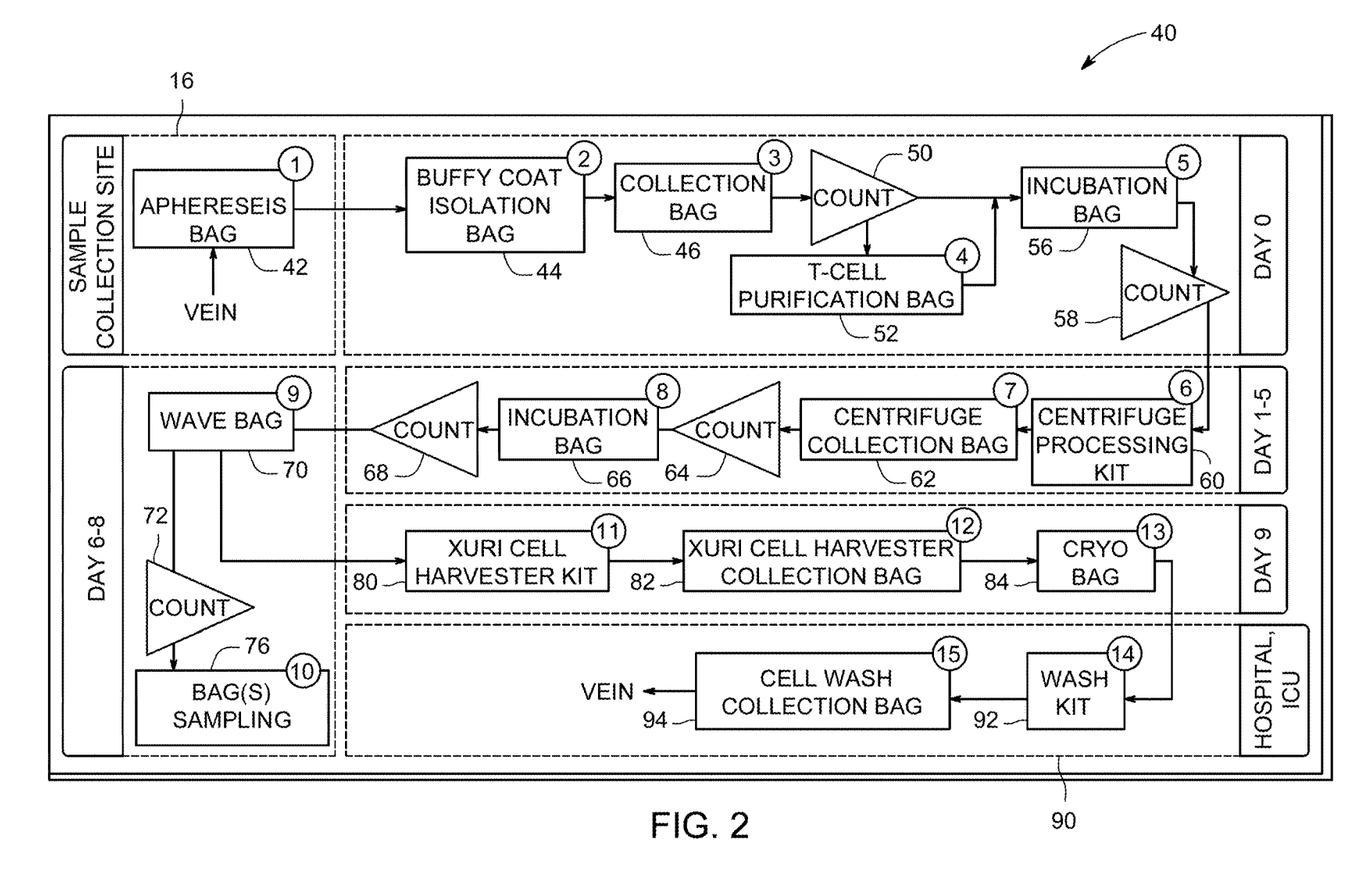
FIG. 2 is a schematic representation of a cell therapy manufacturing process according to an embodiment of the present disclosure.

FIG. 2 is a schematic representation of an example workflow 40 and the numerous sample processing containers (e.g., bags) associated with processing devices, that may be used in conjunction with the disclosed techniques. While the depicted workflow 40 includes specific steps that are performed in conjunction with specific sample processing devices and collection containers that are used to process a patient sample, it should be understood that the depicted workflow 40 is an example, and the disclosed techniques may be used in conjunction with other workflows. At the start of the workflow 40 a sample is collected from the patient at a sample collection facility 16, e.g., a blood-based sample from the patient's vein, and transferred into a sample collection container, depicted here as an apheresis bag 42. The apheresis bag 42 may be used for sample collection involving drawing whole blood from a patient, adding anti-coagulant, and separating blood components. However, it should be understood that other sample collection procedures may also be used, as provided herein. After collection, the workflow proceeds to a cell therapy processing facility. While the depicted embodiment shows that the time frame for cell processing starts at day zero, transport to the cell therapy processing facility may also add to the total therapy preparation time. The workflow 40 then moves onto additional processing steps for cell therapy production. In one example, the sample is transferred from the apheresis bag 42 into a Buffy Coat Isolation Bag 44, in order to process the sample further using one of several types of Buffy coat isolation device. The Buffy coat isolation device 44 may be used in conjunction with a specialized collection bag 46 that contains the sample in a sterile environment during processing by the device 46. Accordingly, the workflow 40 tracks transfer of the sample from the apheresis bag 42 through processing into the collection bag 46. Once separated, the cells are counted 50 with a cell counter and, in certain embodiments, transferred to a T cell purification bag 52 for purification before being transferred to an incubation bag 56 for closed-system culture incubation. As shown, the sample may be counted 58 at additional process points as a quality check.

As depicted, workflow steps may be spaced to permit cell culture incubation and expansion to occur over time in order to achieve a desired cell count. The sample may be transferred to a centrifuge processing bag, 60, for concentration and media replacement using a centrifuge processing device. Once collected into a collection bag 62 and counted 64, the sample may be cultured again in an appropriate culturing container 66, where culturing may be timed based on achieving cell count 68 before using an appropriate bioreactor, e.g., a Xuri™ Cell Expansion System, to propagate the desired cells in a Xuri Cellbag. After counting 72 and analysis of a sample aliquot in a sampling bag 76, the cells are harvested following transfer to a harvesting kit 80 for closed-system processing on a cell harvesting device. Harvested cells are collected in container 82 and then prepared for transfer to cryo bag 84 for cryofreezing prior to shipment to a patient therapy site 90. Once at the therapy site 90, the sample, processed into a cell therapy product, is further processed by, for example in a cell washing device, by transferring to a cell washing kit 92 and transferred to a therapy container 94 for subsequent infusion into the patient as a cellular therapeutic.

Validation of the workflow 40 involves tracking not only the patient sample identity, but the completion of the correct steps, in the correct order, for the correct amount of time, using the correct containers and devices, by the correct personnel. Processing a sample in the workflow 40 may take place over several days, and may involve different personnel depending on the staffing schedule of the cell therapy processing facility. Accordingly, tracking a patient sample involves validation at each step over a period of time. The disclosed techniques provide validation in real-time, so that a process error may be discovered and corrected before sample loss. For certain patients, sample collection is painful and time-consuming, and loss of a sample means that no additional sample can be collected until the patient has recovered from collection. In turn, loss of a sample may result in treatment delays. By achieving an improved percentage of successful therapy product generation from incoming samples, patient treatment delays may be reduced.

Certain embodiments of the disclosure provide improved validation and tracking of patient samples as they are processed to generate a cell therapy product. In certain embodiments, the workflow is implemented using a control system 100, implemented as a central controller 104 as shown in the block diagram of FIG. 3. The central controller 104 may include a processor 106, and a memory 108 storing instructions executable by the processor 106. The memory 108 may include one or more tangible, non-transitory, machine-readable media. By way of example, such machine-readable media can include RAM, ROM, EPROM, EEPROM, CD-ROM, or other optical disk storage, magnetic disk storage or other magnetic storage devices, or any other medium which can be used to carry or store desired program code in the form of machine-executable instructions or data structures and which can be accessed by the processor 106 or by any programmed general purpose or special purpose computer or other machine with a processor. The central controller 104 may also include communications circuitry 114 and/or input and output circuitry 112 to facilitate communication with other components of the system 100. Further, the central controller 104 may include a display 110 that provides a graphical user interface for operator interaction. The central controller 104 may be implemented at least in part on a cloud storage network.

Figure 3:
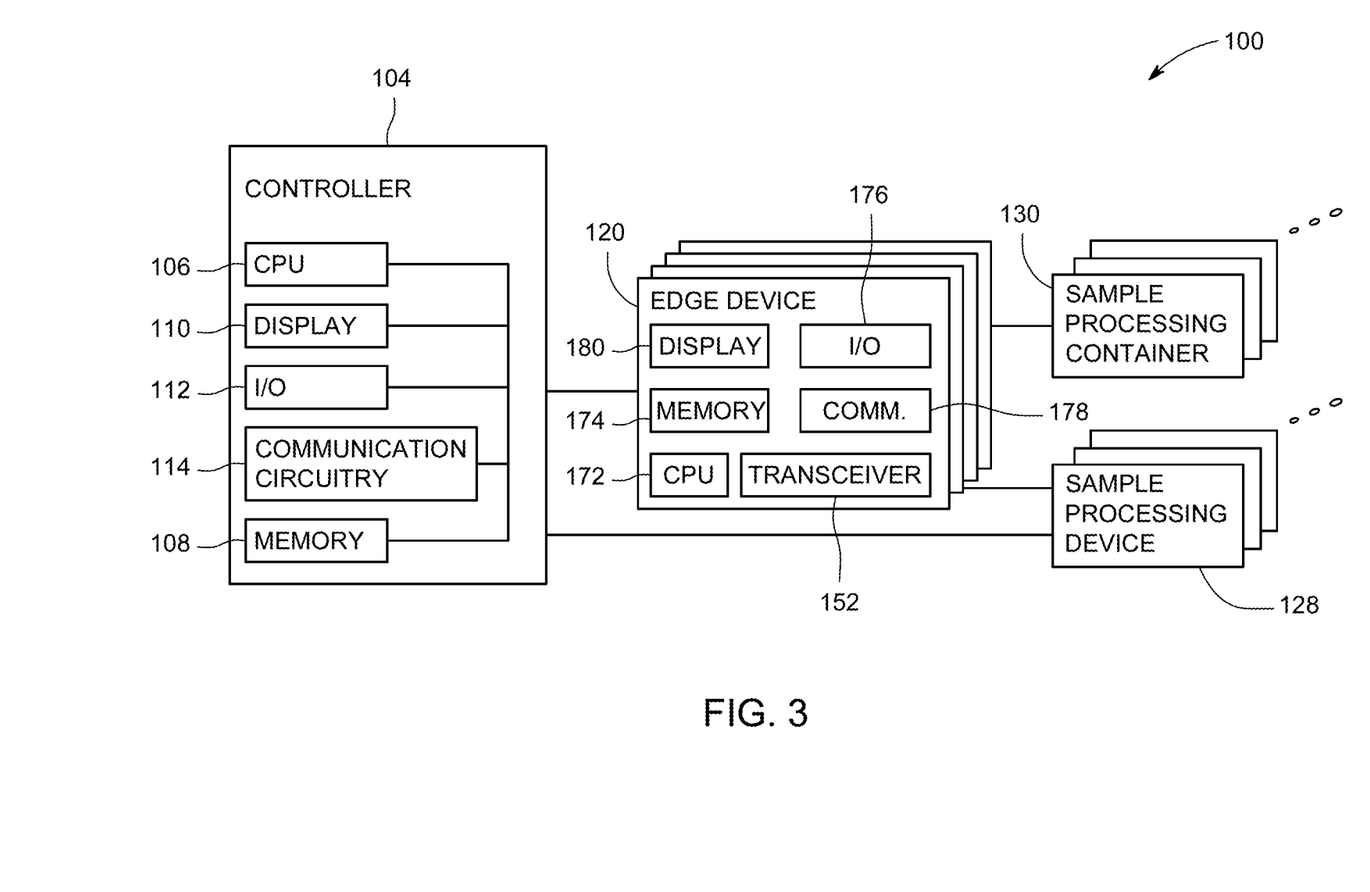
FIG. 3 is a block diagram of a cell therapy manufacturing control system according to an embodiment of the present disclosure.

A reader 120 is configured to read information via receiver or transceiver hardware 152. The reader 120 may be co-located with the sample processing device 128 and any sample within a sample processing container 130 that is being operated on by the sample processing device 128. Alternatively or additionally, the reader may be co-located with a sample processing station that does not include a sample processing device 128. A central processing unit 172 of the reader 120 may execute instructions stored in a memory 174. Further, the reader 120, in certain embodiments, may be implemented as an edge device. For example, when implemented as an edge device, the reader 120 may provide an entry point into a network and may include hardware circuitry such as routers, routing switches, integrated access devices (IADs), multiplexers, and a variety of metropolitan area network (MAN) and wide area network (WAN) access devices. The reader 120 may include onboard input/output circuitry 176, communications circuitry 178, and a display 180 that provides a graphical user interface for operator interaction. The reader 120 may execute routines to translate received signals that are in a particular protocol, such as an RFID protocol, into an http protocol prior to transmission to the controller 104.

Figure 4:
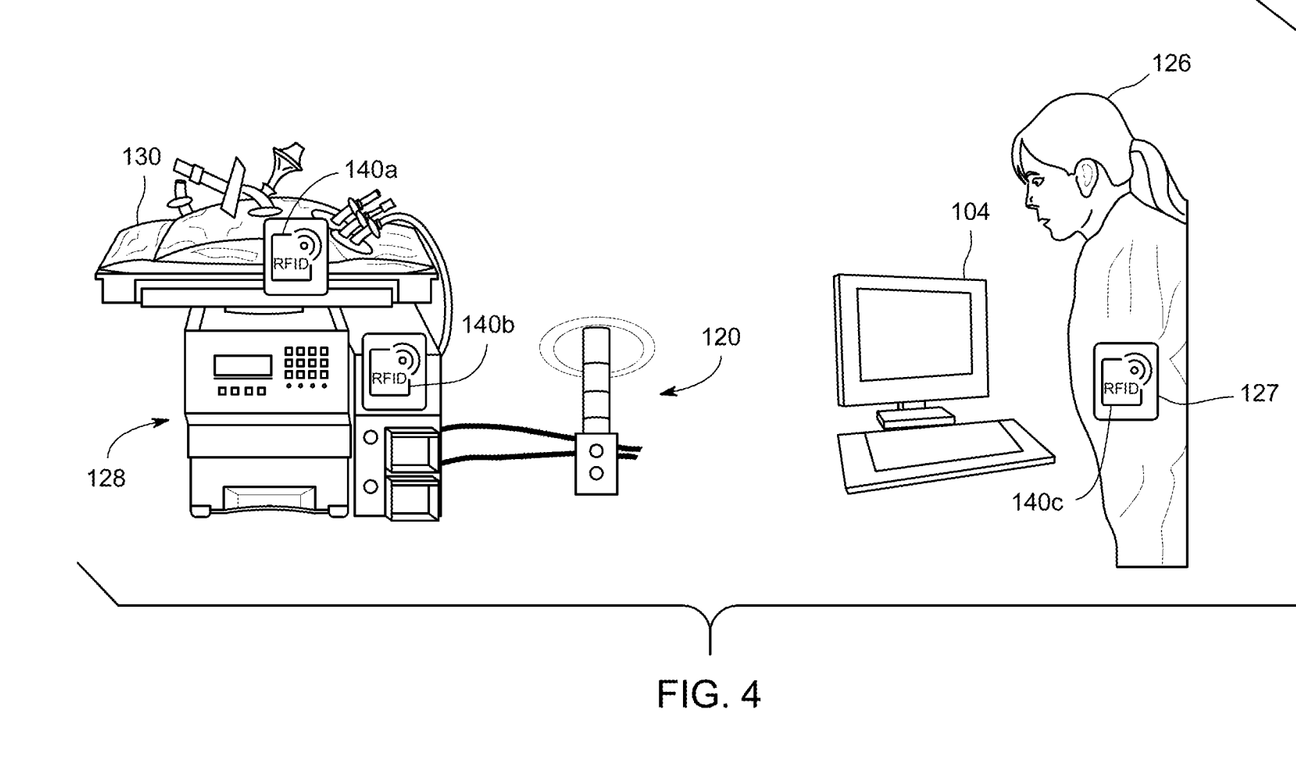
FIG. 4 is a schematic representation of a cell therapy manufacturing control system according to an embodiment of the present disclosure.

FIG. 4 is a schematic diagram of a work station or work area within a sample processing facility. The work area represents an area for completing a step of a cell processing workflow as provided herein. During processing of a sample, the sample is transferred into the appropriate sample processing container 130 for use with the sample processing device 128. The reader 120 reads information from tracking devices 140(*a-c*), shown as RFID tags, e.g., a tracking device 140*a* on the sample processing container 130 and, in certain embodiments, a tracking device 140*b* on the sample processing device. The associated information derived from the sample processing container's tracking device 140*a* may include the identity of the patient sample. In embodiments, the information may be directly stored on the tracking device 140*a-c*. In another embodiment, the tracking device 140 may store a unique identifier that, when used to query a database stored in the central controller 104, is associated with additional data. For example, if the tracking device 140*a* is associated with the patient sample, the stored unique identifier may be associated with a patient name, patient information, medical history information, a patient number, sample intake information, and the sample processing protocol associated with the patient sample. The information may also include identification information or specifications of the sample processing container 130. In one embodiment, the sample processing container includes its own label or tag with container identification information that may be read by the reader 120. However, such information may additionally or alternatively be provided via the tracking device 140*a*. The information from the sample processing device 128 may include device identity and/or operating parameters.

The system 100, in the illustrated embodiment, includes one or more readers 120 that read identification information associated with operators 126, e.g., via operator badges 127 and that in turn pass the identification information to the controller 104. The identification information may be a unique identifier associated in a database on the central controller 104 with an operator name or employee number as well as other operator information, including staffing schedules, assigned samples, certification or training information, etc. In addition, the reader 120 may read information from a co-located sample processing device 128, which may be an incubation device, a culture device, a purification device, a separation device, a storage device, etc. The reader 120 may read information from any location or assets used in the manufacturing process for a particular processing step. The associated information may include information associated with (e.g., directly stored or queried in a database stored on the controller 104) device identification and parameters, such as operating parameters, as well as device location within the manufacturing facility. In another embodiment, an individual reader 120 co-located with the sample processing device 128 may provide the sample processing device information without reading it from the sample processing device 128 each time the device is used. That is, because the sample processing device 128 may remain the same even as the patient and/or operator changes, the sample processing device information may be stored in a memory of the device 128 and/or reader 120 for transmission to the controller 104 along with operator or patient sample information. While in the depicted embodiment, the controller 104 is implemented as a separate device from the reader 120 and the sample processing device 128, it should be understood that certain functionalities of the controller 104 and the reader 120 may be incorporated into the sample processing device 128. The reader 120 may also read information from identifier tags associated with one or more sample processing containers 130.

The reader 120 may be associated with a device 128 or a location that may or may not include a device 128. Each dedicated reader 120 may be associated by the controller 104 at system setup such that the controller 104 assigns or associates the signals received from each reader 120 to the appropriate location. In another embodiment, the location of the received signals and the associated sample is determined based on reading the tag 140b associated with the device 128.

Figure 5:
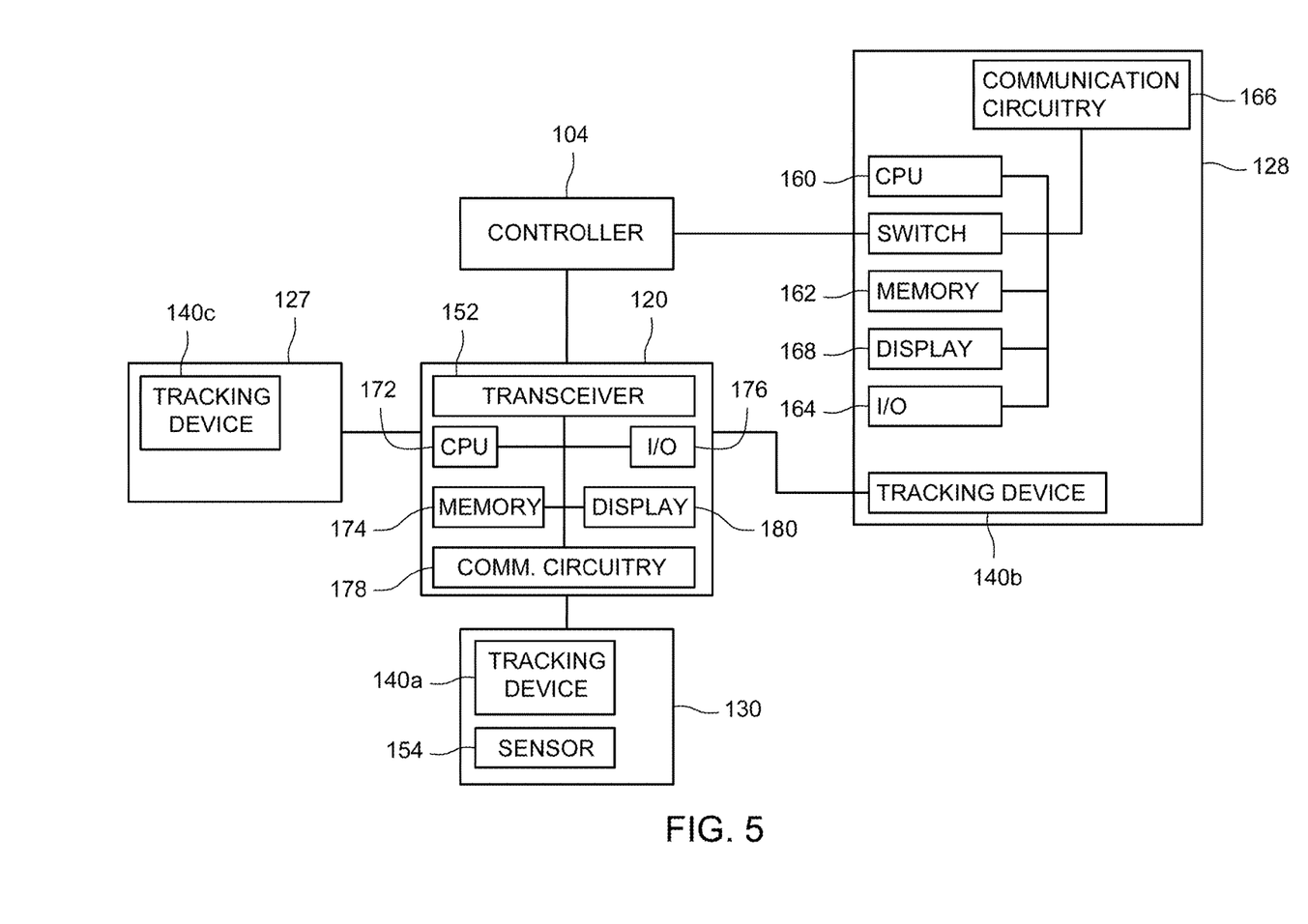
FIG. 5 is a block diagram of an cell therapy manufacturing g control system according to an embodiment of the present disclosure.

The information read from the tracking devices 140 by the reader 120 is sent to the controller 104 for confirmation that the workflow associated with the patient is being followed, which may be indicated via a notification device 150. The controller 104 may be located within the work area and may, in certain embodiments, include its own dedicated reader 120 to prevent the operator from having to badge in within a clean room where the sample is located. In other embodiments, the controller 104 is remote from the work area. Further, the reading by the reader 120 may be in a generally hands-free manner. Accordingly, the tracking device 140 may be configured to be read by the reader 120 over a short or medium range to promote hands-free interaction, which in turn provides greater usability in sterile clean room environment where operators are fully gowned in personal protective equipment. Further, in certain embodiments, the reader 120 and the tracking device 140 may be configured as a passive RFID tag to communicate at 13.56 MHz, a frequency recommended for use with blood and cellular materials, and commonly found in the blood banking industry FIG. 5 is a block diagram of certain components of FIG. 4. In the depicted embodiment, the controller 104 may be implemented as a workstation in the location of the sample processing device 128. Additionally or alternatively, the system includes a remote central controller 104. The sample processing device 128 is a device that operates on a patient sample according to a workflow of a manufacturing protocol. the sample processing device 128 is typically used to process many samples. Each sample is housed within a sterile and disposable processing container 130 to avoid contamination, and the sample processing container 130 may be configured in size and shape to be used with the sample processing device 128. Accordingly, different steps of the workflow may involve sample transfer between different sample processing containers 130 as different sample processing devices 128 are used over the course of manufacturing the cell therapy product.

In embodiments in which the sample processing device 128 is an incubator, the device 128 may be configured to maintain a certain temperature or temperature range over a particular time period. In other embodiments, the sample processing device 128 may include mechanical rockers or inlet and outlet ports to provide cell culture media. The sample processing device, when configured to separate the sample, may be configured to spin or otherwise separate the sample into desired products, and/or remove separation products. Accordingly, the appropriate sample processing containers 130 for each respective sample processing device 128 may include appropriate ports that couple to features on the sample processing device 128 to facilitate flow into or out of the sample processing container 130. The sample processing container 130 may also include one or more feedback features, such as a sensor 154, to provide data on the workflow step. In one embodiment, the sensor 154 is a thermistor that provides data about temperature conditions of an incubation.

The reader 120 is co-located with the sample processing device 128 and any sample within a sample processing container 130 that is being operated on by the sample processing device 128. In one embodiment, a receiver or transceiver 152 of the reader 120 reads information from tracking devices 140 associated with one or more of the sample processing device 128 (tracking device 140b), the operator badge 127 (140c), or the sample processing container 130 (140a). The tracking device 140 may be one of a radio frequency identifier (RFID), a barcode label, or a magnetic stripe tag embedded in a tag. The tracking device 140 is wirelessly detectable in the sense that it is detectable by the reader 120 without requiring that a fixed-wire connection be established. For example, the tracking device 140 may be a passive RFID tag, and the reader includes a transceiver that may, for example, send an activation signal to the RFID tracking device 140 to activate an antenna in the tracking device 140 to emit an RF signal when in the field of the reader 120. n active tag Each sample processing device 128 may include a central processing unit 160, and a memory 108 storing instructions executable by the processor 160. The processor 160 controls operation of the sample processing device 128, e.g., which may include temperature control, rocking speed, motor speed, etc. The sample processing device 128 may include input/output circuitry 164, communications circuitry 166, and a display 168 that provides a graphical user interface for operator interaction. In certain embodiments, the sample processing device may include a mechanical switch 170 that permits or prevents operation of the device based on workflow validation. A central processing unit 172 of the reader 120 may execute instructions stored in a memory 174. Further, the edge device 120 (FIG. 3) may include onboard input/output circuitry 176, communications circuitry 178, and a display 180 that provides a graphical user interface for operator interaction.

The sample processing device 128 and/or the reader 120 may also include a clock, and the signals provided to the controller may include time information. For example, checking in (i.e., reading) a sample processing container 130 to the sample processing device 128 may start a clock, and checking out may stop the clock. Checking out may be another reader swipe or may be in the form of checking in at the next sample processing device 128. In this manner, time at each sample processing device 128 may be tracked.

Figure 6:
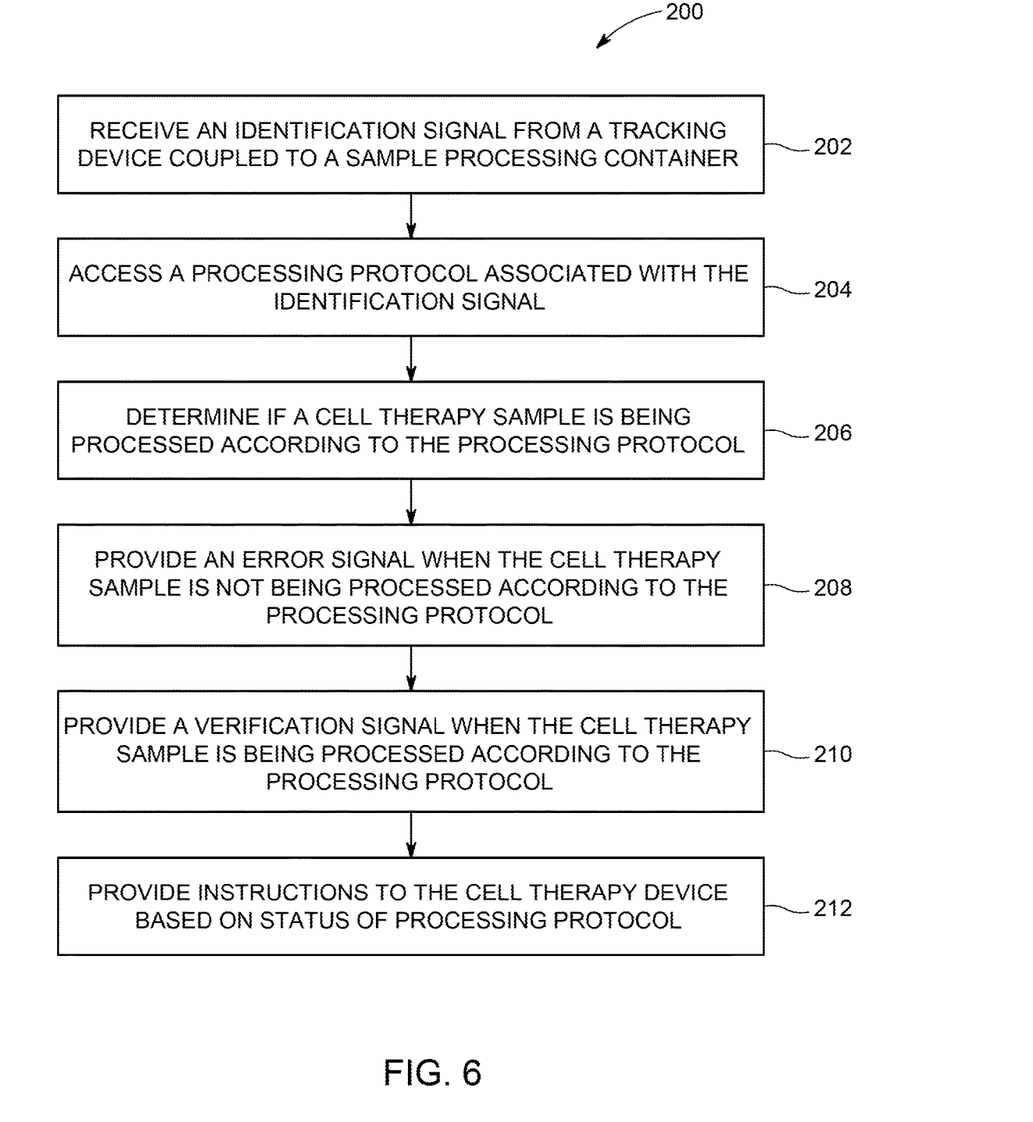
FIG. 6 is a flow diagram of a cell therapy process verification according to an embodiment of the present disclosure.

FIG. 6 is a flow diagram of a method 200 of validating a workflow. The method 200 may be repeated at various individual work areas within a cell processing facility during processing of a single patient sample. The method may be performed at least in part by a control system 100 (see FIG. 4). At the start of the method 200, an identification signal from a tracking device coupled to a sample processing container is received (block 202). The identification signal is associated with a unique patient sample in the controller, and may reference identification information such as a patient or sample number or other information to associate the sample processing container, and the enclosed sample, with a particular patient. For example, the identification signal may include a unique identifier that is associated with the patient/sample information (and, for example, the processing protocol associated with or assigned to the patient) in a database of the controller. Accordingly, upon receipt of the unique identifier from the identification signal, a user of the workflow management system, e.g., an operator of the control system, would initially assign the patient sample to a desired processing protocol. In turn, during tracking of the sample, the identification signal is associated with the assigned protocol. In certain embodiments, the identification signal may include identification information for the sample processing container. In the alternative, the sample processing container may include a separate tracking device that provides a separate identification signal.

Based on the identification signal that identifies a patient sample, the appropriate processing protocol may be accessed (block 204) and the system may determine if the cell therapy sample is being processed according to the processing protocol (block 206). Based on whether the processing protocol is being followed, an error signal (block 208) or a verification signal is provided (block 210), and instructions to the sample processing device are provided based on the status of the processing protocol (block 212). For example, the instructions may permit or prevent operation of the sample processing device. The instructions to permit operation of the sample processing device may involve operation of a hardware switch that controls power to the sample processing device. In another example, the instructions to permit operation may involve providing a drive signal to hardware components of the sample processing device, such as a motor, a heater, a rocker, etc. In another example, the instructions to permit operation of the device may involve providing instructions to the operator or to the device to execute routines associated with the operation of the device. Preventing operation of the device may also involve operation of the hardware switch or the lack of an appropriate drive signal to the mechanical components. In another embodiment, preventing operating of the device may involve instructions not to execute routines associated with operation of the device.

In a specific embodiment, a reader that receives the identification signal is associated with a dedicated sample processing device. The reader may read the information related to the sample processing device from an associated tracking device. In another embodiment, the central controller may provide the information from a memory. The method 200 may provide a verification signal when the sample is being processed according to the processing protocol when, for example, when the correct patient sample in the correct sample container is placed in the correct sample processing device at the correct step in the processing protocol. However, when the sample processing device is not part of the cell processing protocol, the method 200 may provide an error signal that the processing protocol is not being followed. In another example, the system may base the determination on an ordered sequence of previous identification signals and process information. For example, when a particular sample processing device is being used out of sequence, an error signal may be provided. In another embodiment, the method 200 may determine if a protocol is being followed based on an expected time at each step. For example, an expansion step associated with a sample processing device may be associated with a particular time or achievement of a performance metric (e.g., cell count, viability). If the cell processing container is removed prematurely, the method 200 may prevent advancement to the next step of the processing protocol. The sample processing device may provide operating information to the system (e.g., controller 104, see FIG. 5) to determine if the processing protocol is being followed. If an operator programs improper parameters into the device, an error signal may be provided.

Additionally or alternatively, the method 200 may use a sample processing container identity as part of a determination of whether the sample is being processed according to the processing protocol. For example, when the reader is associated with a particular sample processing device or manufacturing location, the method 200 may determine that the sample processing container should be used with the device or location and provide a verification signal, or that the sample processing container is the wrong type of container for the device and provide an error signal. Such an error may be the result of an operator failing to transfer a sample to a new processing container. In this manner, the use of the improper container is caught before operation of the device such that the sample may be recovered before any processing with the wrong device takes place. Recovery may involve transferring the sample to the appropriate sample processing container. As provided herein, an individual sample processing device (i.e., sample processing device 128, see FIG. 5) may have an operator interface that permits operator control. However, in certain embodiments of the disclosure, the devices may be configured such that an operator cannot override instructions to prevent operation of the device in the event of an error signal until appropriate steps are taken to clear the error. In one embodiment, a new identification signal from the appropriate cell processing container may clear the error signal and provide a verification signal that the error is cleared. The system may retain a record of the error signal as a training tool to identify processing errors.

A signal from an operator badge may also be used to determine if the correct patient sample is being processed by the correct operator. For example, each operator badge may be associated with a unique patient sample, or a set of unique samples. If the identification signal is not from a patient sample associated with the operator badge, an error signal is provided. In this manner, an operator is prevented from picking up the wrong sample from a previous step and moving forward. In another example, the method 200 may be used to associate particular operators with training and/or certifications with the appropriate protocols or devices.

Accordingly the verification and/or error signals may be based on one or more identification signals from one or more of the sample processing containers, the sample processing device and/or the operator. Other sources that are provided to determine the verification and/or error signals may be based on feedback from feedback devices (e.g., sensors 154, see FIG. 5).

Figure 7:
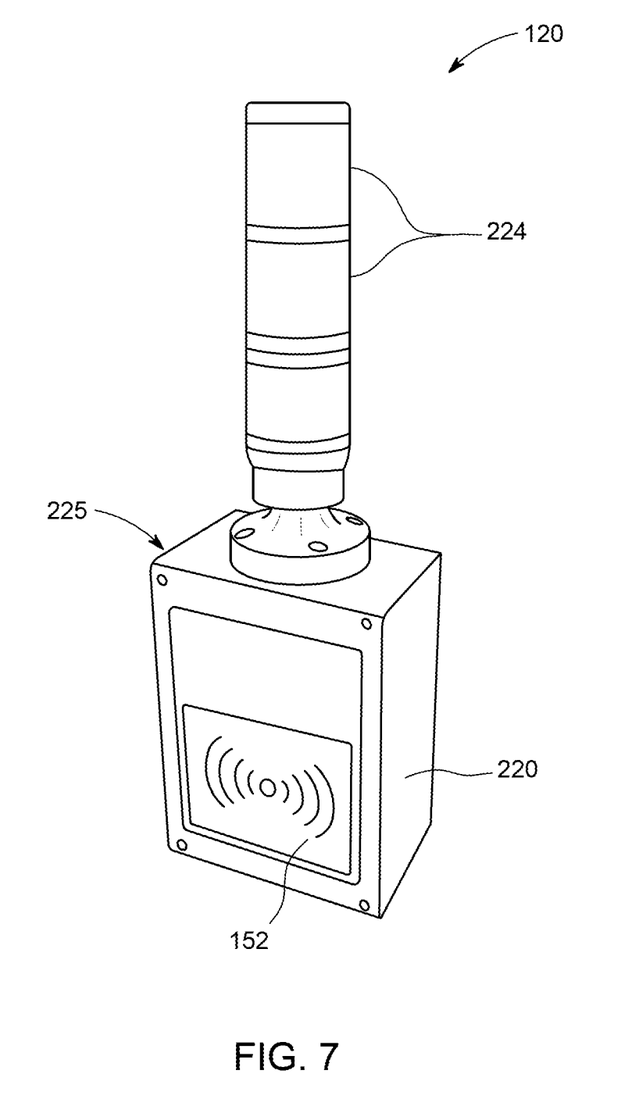
FIG. 7 is an example of an integrated edge device according to an embodiment of the present disclosure.

FIG. 7 is an embodiment of a reader 120, which may be implemented as an edge device reader 120 that may be used in conjunction with the disclosed techniques. The reader 120 includes a receiver or transceiver 152 and an audio or visual notification device, such as one or more light sources 224. Alternatively or additionally, the reader 120 may include a speaker. For example, the light sources 224 may include a red light that lights only when an error signal is provided and a green light that lights only when a verification signal is provided. In another embodiment, the notification device may emit a warning tone when an error signal is provided and may be silent/emit no tone when a verification signal is provided. It is contemplated that for critical steps in the processing protocol where real-time tracking is desired, a dedicated reader 120 would be installed, including at processing devices or manufacturing areas. The manufacturing areas could include a sample preparation area, sample container labeling (kitting) station, sample quality testing lab, or cryofreezers for final storage. As the operator moves a sample into the work area, the operator's badge and the tracking device on the sample processing container is read by the reader 220. In certain embodiments, the range of the reader 220 is confined to the work area to prevent reading of badges/sample containers that are not associated with the work area. However, in other embodiments, a work area is in a separate clean room. The reader 120 may receive the error or verification signals from a controller (i.e., controller 104, see FIG. 5) that in turn result in the light source activation. The light sources 224 provide a visual notification to alert the operator to any errors in the processing protocol in real time.

The reader 120 may be implemented with a unitary housing 225 such that the components of the reader 120 e.g., the transceiver, processor, memory, notification device, etc., may be easily installed by an operator in a plug-and-play manner and allow easy installation at multiple locations for example the manufacturing facility, the sample collection site, and the site of therapy administration. In one embodiment, communications circuitry of the reader 120 may permit wireless coupling to a sample processing device as well as a central controller. In another embodiment, the reader 120 may be configured to drop in to a dedicated port or docking station on a sample processing device.

Upon installation, the reader 120 may be coupled to or associated with a dedicated sample processing device. In one embodiment, the reader 120 may receive information (e.g., machine identification, location, specifications, operating information) about the sample processing device via a direct or wireless connection. The information may be stored in a memory of the reader 120 and may be co-transmitted with signals read from sample processing containers to a central controller 104. In another embodiment, the reader 120 acts as a pass-through and sends information on to the controller 104. The coupling to the sample processing device may be automatic, based on a proximity or zone relationship, or may be via manual input by an operator. The reader 120 may be configured to operate in conjunction with a plurality of different types of sample processing devices. For example, the reader 120 may store different operating modes in a memory of the device and may select the appropriate operating mode based on the coupled sample processing device.

In one embodiment, an operating mode for a sample processing device may include instructions to activate the transceiver 222 to scan for tracking devices at certain time intervals, while the operating mode for a different sample processing device may require scanning more frequently for tracking devices. An inventory mode may involve still more frequent scanning. Accordingly, the coupling to a particular sample processing devices activates instructions to implement the appropriate operating mode for the reader 120.

Figure 8:
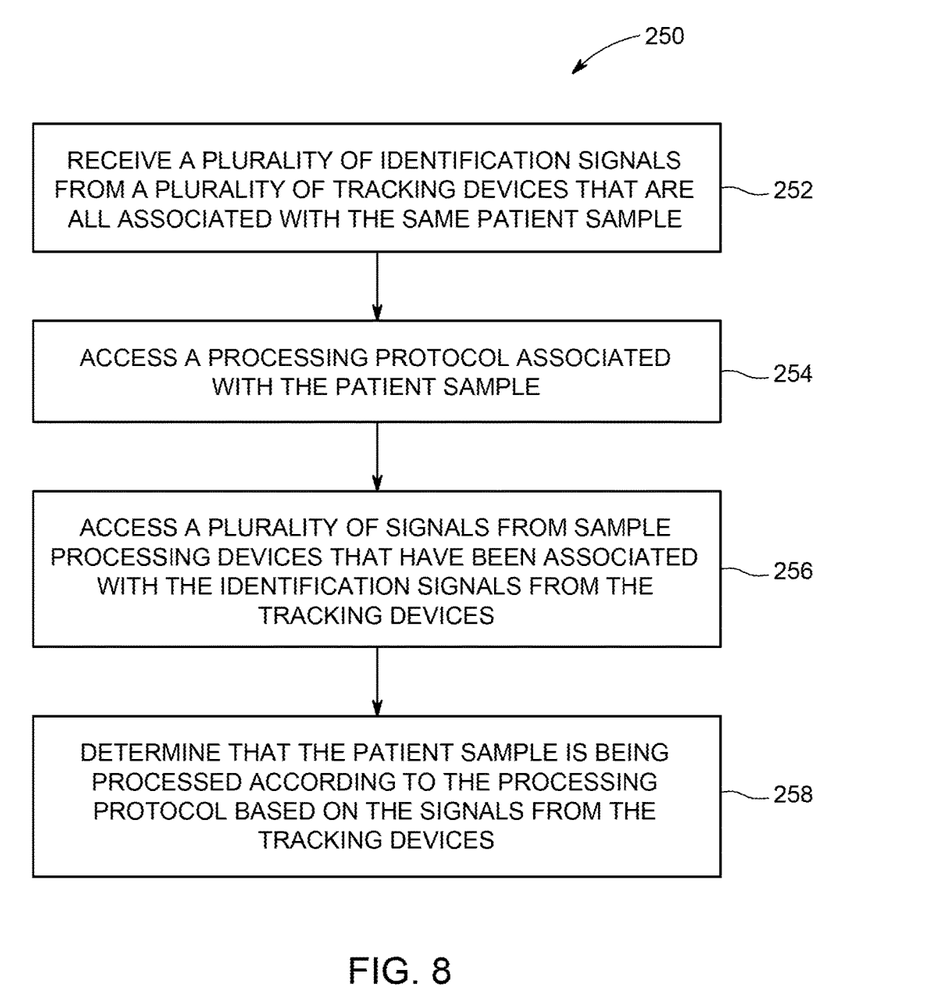
FIG. 8 is a flow diagram of a cell therapy manufacturing control process according to an embodiment of the present disclosure.

The system (i.e., system 100, see FIG. 3) tracks and validates a cell processing protocol that takes place over a period of time and that involves many individual workflow steps. Accordingly, in certain embodiments, a method 250 (FIG. 8) may validate all or part of the workflow, either in real-time or post-processing, based on feedback from a plurality of identification signals from a plurality of tracking devices associated with a patient sample (block 252). The method 250 accesses the processing protocol associated with the patient sample (block 254) as well as the signals from the sample processing devices (block 256) that are associated with each step of the workflow to determine that the sample is being processed according to the processing protocol (block 258). For example, as each sample is badged into a work area, the identification signal is sent from an individual reader along with a signal such as a location or device signal that includes identification information for the work area and/or the associated sample processing device. In one embodiment, this information may be stored in a memory if the manufacturing location/device does not move. The time stamp of the identification signal and the device or location signal may be used to validate the processing protocol. As each processing protocol is generated during sample intake, the protocol may include estimated process times or performance metrics (e.g., cell count) for each step. If the time stamp of a signal is out of sequence relative to other signals or outside of the target time, an error signal is generated. In this manner, global process deviations may be detected. For example, a sample may be checked in to a work area in a verified step. However, if the sample is left in the processing device for too long, the error is caught at the next step when the next check in is outside of an expected time. Once the error is detected, sample recovery measures may be initiated. For example, a cell count or viability may be assessed. If the cell count or viability is appropriate, the sample progresses through the processing protocol. In other embodiments, future processing steps may be adjusted based on the error. For example, if the cell count is low, a longer time duration for the sample cell expansion step(s) may be appropriate. The validation or record of the process may be stored for access during an audit or may be transmitted to the therapy site or a regulatory body as part of the validation process.

Figure 9:
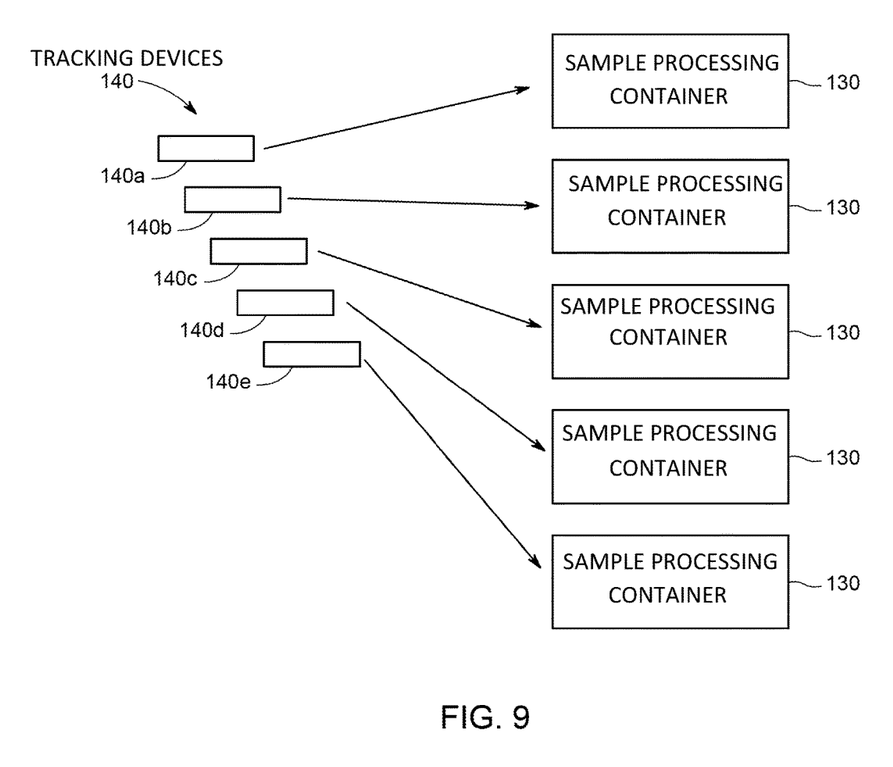
FIG. 9 is a schematic representation of labeled sample container according to an embodiment of the present disclosure.

FIG. 9 is a tracking device kit that includes a plurality of tracking devices 140 that may be applied to sample processing containers 130 during a cell processing workflow. Each kit of tracking devices 140 is associated with a unique patient sample such that reading each tracking device 140 provides a signal that contains identification information for the patient sample.

During sample intake, the kit is generated ahead of initiation of the work flow. Accordingly, generation of the kit may include writing the identification information of the unique patient sample to each tracking device 140. Depending on the processing protocol, each tracking device 140 may be the same or different. For example, it may appropriate for the tracking devices 140 to be adhesively applied to the sample processing containers 130. However, certain workflow steps may be inappropriate for adhered labels, such as water bath steps, and the tracking devices 140 may be generated as a strap or other form factor configured to be associated with a sample processing container 130. In one embodiment, the tracking device 140 is encapsulated in a film to prevent water infiltration. In other embodiments, certain tracking devices may be in the form of adhesive labels (e.g. tracking devices 140*a-c*) while other tracking devices are printed on or otherwise integrated into an operator badge. Further, the information may be stored on an operator badge (e.g., badge 127, see FIG. 4). If an individual operator is processing several patient samples, sample intake may involve writing the unique sample identification to the badge or badges to be stored among a set of patient sample identification information. The kitting may be accomplished in conjunction with a handheld reader to verify appropriate labeling.

Figure 10:
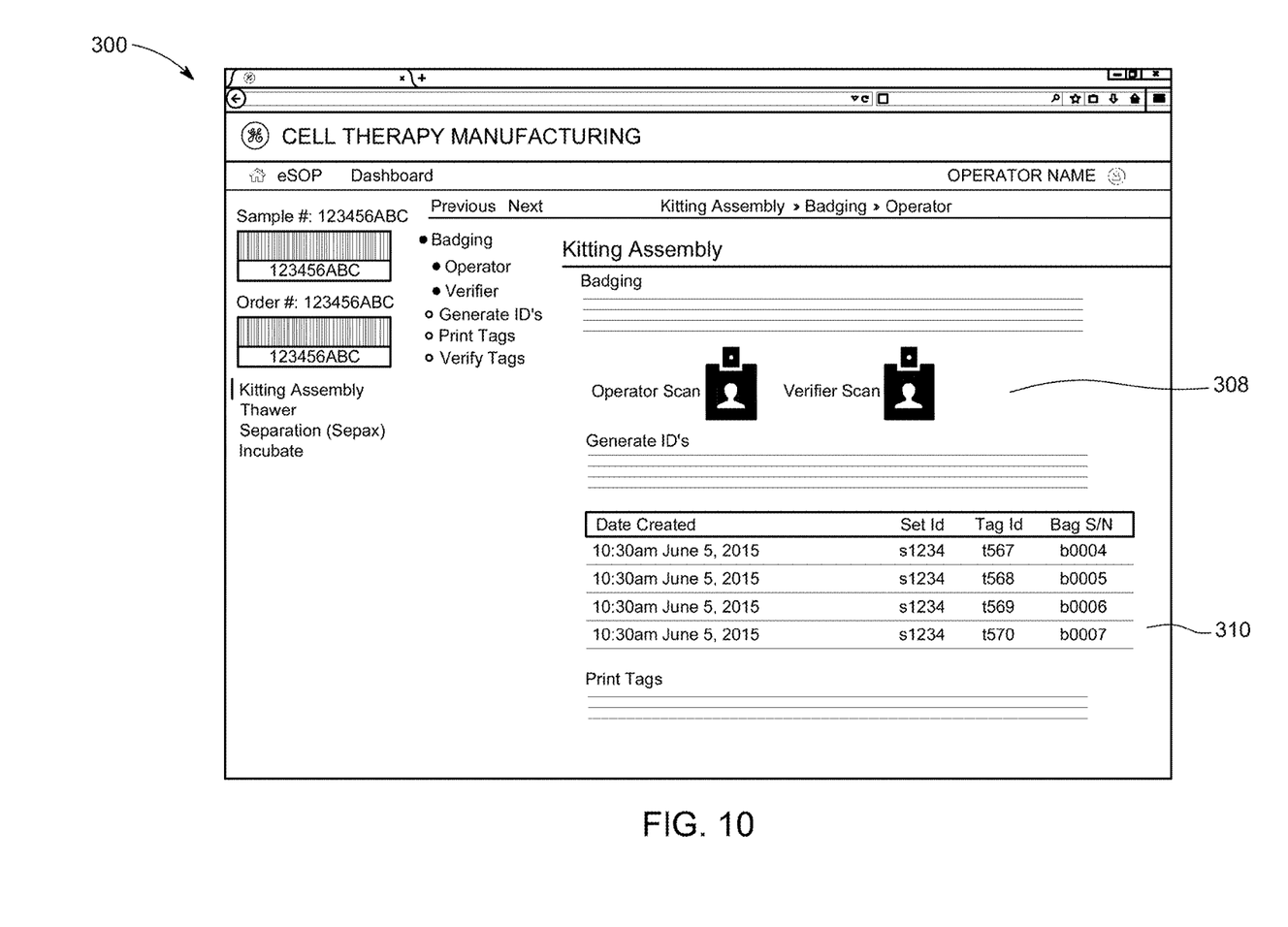
FIG. 10 is an example of a user interface for operator interaction with a control system used in a cell therapy manufacturing control process according to an embodiment of the present disclosure.

FIG. 10 is an example user interface display 300 that may be used to reduce errors and prevent protocol deviations during processing of a patient's cell therapy sample. The illustrated display 300 may be used in conjunction with the system 100 (see FIG. 3) to generate a tracking device kit system. At sample intake, an user is provided menu sections 308, 310 for associating a patient cell therapy sample with operator badges 308 and identification information for tracking devices 310. Other display screens of the user interface may provide workflow instructions, sample tracking information, real-time process updates, etc.

Technical effects of the invention include improved sample tracking and throughput for cell therapy production. The disclosed techniques facilitate improved compliance by providing notifications when a deviation has occurred to allow an operator to correct the deviation real-time. Further, control of the processing equipment may be dependent on adherence to prior steps in the workflow. Such techniques may be used to improve throughput and quality of cell therapy production.

This written description uses examples to disclose the invention, including the best mode, and also to enable any person skilled in the art to practice the invention, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A cell therapy manufacturing tracking system, comprising:
   a cell therapy sample;
   a sample container configured to hold the cell therapy sample;
   a reader co-located with a sample processing location and configured to receive an identification signal from a first tracking device coupled to the sample container;
   a sample processing device configured to process the cell therapy sample;
   a second tracking device coupled to the sample processing device;
   a controller operatively coupled to the reader and configured to:
      access a cell therapy processing protocol associated with the identification signal upon receipt of the identification signal;
      determine if the cell therapy sample is being processed according to the processing protocol;
      provide an error signal to the sample processing device when the cell therapy sample is not being processed according to the processing protocol;
      provide a verification signal to the sample processing device when the cell therapy sample is being processed according to the processing protocol;
      prevent continuing operation of the sample processing device based on the error signal; and
      permit continuing operation of the sample processing device based on the verification signal;
   wherein one or both of the error signal and the verification signal is based on signals from the first tracking device coupled to the sample container, the second tracking device coupled to the sample processing device, and a third tracking device coupled to an operator badge.

2. The system of claim 1, wherein the sample processing location is associated with a sample processing device.

3. The system of claim 2, wherein the controller is configured to determine if the cell therapy sample is being processed according to the processing protocol based on receiving one or more signals representative of a completion of prior steps before a step involving the sample processing device.

4. The system of claim 2, wherein the sample processing device comprises a switch configured to permit operation of the sample processing device only when the verification signal is provided.

5. The system of claim 1, wherein the controller is configured to start a clock when determining that the verification signal is provided.

6. The system of claim 5, wherein the controller is configured to stop the clock upon receipt of a second signal from the tracking device or from an operator.

7. The system of claim 1, wherein the controller is configured to provide an error message when a step associated with the tracking device is performed and is not part of the processing protocol or varies from a step sequence of the processing protocol.

8. The system of claim 1, wherein the controller is configured to determine if the cell therapy sample is being processed according to the processing protocol based on the identifier signal associated with the sample processing container.

9. The system of claim 8, wherein the controller is configured to provide an error message when a step involving the sample processing container is not part of the processing protocol or varies from a step sequence of the processing protocol.

10. The system of claim 9, wherein the controller is configured to provide an error message when the sample processing container or the cell therapy sample used together with the sample processing device is not part of the processing protocol.

11. The system of claim 1, comprising a switch controlling operation of the sample processing device, wherein the controller is further configured to provide instructions associated with a processing protocol status, wherein the switch is configured to prevent operation of the sample processing device when the error signal is provided and based on the instructions.

12. The system of claim 1, wherein the tracking device is an RFID tag.

13. The system of claim 12, wherein the controller is further configured to provide instructions associated with a processing protocol status, and wherein, upon receiving the instructions, the sample processing device is configured to pause or prevent execution of routines for operation of the sample processing device.

* * * * *